United States Patent [19]
McPhee

[11] Patent Number: 5,665,070
[45] Date of Patent: Sep. 9, 1997

[54] INFUSION PUMP WITH MAGNETIC BAG COMPRESSION

[75] Inventor: Charles J. McPhee, Huntington Beach, Calif.

[73] Assignee: I-Flow Corporation, Irvine, Calif.

[21] Appl. No.: 374,877

[22] Filed: Jan. 19, 1995

[51] Int. Cl.⁶ ................................ A61M 37/00
[52] U.S. Cl. .................. 604/131; 604/132; 604/133; 604/134; 604/141; 604/151; 604/153; 604/246; 222/95; 222/105; 222/336
[58] Field of Search .................. 604/131–134, 604/141, 151, 153, 246; 222/95, 105, 336

[56] References Cited

U.S. PATENT DOCUMENTS

| | | | |
|---|---|---|---|
| 119,996 | 6/1871 | Randall . | |
| 1,425,191 | 8/1922 | Garbarini . | |
| 2,240,307 | 4/1941 | List | 103/53 |
| 2,849,159 | 8/1958 | Kaufmann | 222/309 |
| 3,768,931 | 10/1973 | Willis, Jr. | 417/322 |
| 3,842,440 | 10/1974 | Karlson | 3/1 |
| 4,274,407 | 6/1981 | Scarlett | 128/213 |
| 4,302,854 | 12/1981 | Runge | 3/1.7 |
| 4,360,019 | 11/1982 | Portner et al. | 128/213 |
| 4,444,548 | 4/1984 | Andersen et al. | 417/63 |
| 4,447,232 | 5/1984 | Sealfon et al. | 604/134 |
| 4,488,099 | 12/1984 | LaForge et al. | 318/561 |
| 4,557,726 | 12/1985 | Reinicke | 604/67 |
| 4,594,058 | 6/1986 | Fischell | 417/413 |
| 4,907,723 | 3/1990 | Katz | 222/105 |
| 5,232,439 | 8/1993 | Campbell et al. | 604/28 |
| 5,242,406 | 9/1993 | Gross et al. | 604/132 |
| 5,328,477 | 7/1994 | Sitko | 604/134 |
| 5,330,431 | 7/1994 | Herskowitz | 604/153 |

*Primary Examiner*—Sam Rimell
*Assistant Examiner*—Robert V. Racunas
*Attorney, Agent, or Firm*—Klein & Szekeres, LLP

[57] ABSTRACT

An infusion pump for providing a pressurized liquid flow from a collapsible, deformable reservoir bag includes a magnetically actuated pressurizing member that applies a pressure to the bag in response to the force of magnetic attraction applied by a magnet. In several embodiments, a bag is seated on a platen of magnetizable metal, and a magnet with a compressing surface is mounted for movement toward and away from the platen. As the magnet is moved toward the platen by the force of magnetic attraction, the bag is pressurized between the magnet and the platen. The magnet may be spring biased either toward or away from the platen to alter the relationship between the decreasing volume of the bag and the pressure applied to it, by compensating in a known manner for the change in the magnitude of the magnetic force with the distance between the magnet and the platen. In another embodiment, a pair of magnets are pivotably attached to opposed edges of the platen, so as to be pivotable, "drawbridge" style, toward and away from the platen. In still another embodiment, a fixed magnet attracts a magnetizable metal plate which is connected, by a pivoting linkage, to a pressure plate. A reservoir bag is placed between the pressure plate and a fixed surface. As the metal plate moves toward the magnet, the linkage causes the pressure plate to move toward the fixed surface, pressurizing the bag therebetween.

30 Claims, 3 Drawing Sheets

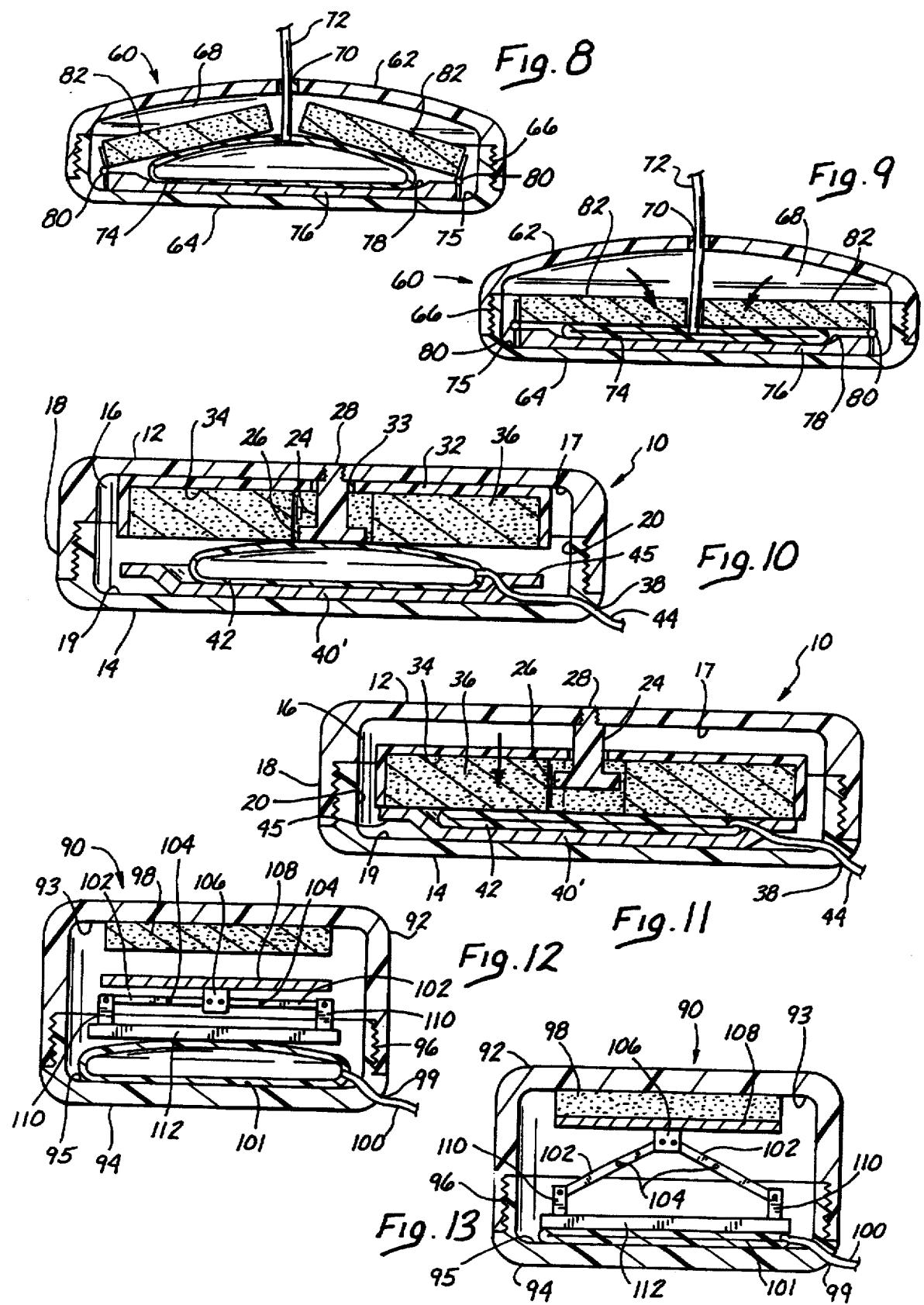

INFUSION PUMP WITH MAGNETIC BAG COMPRESSION

BACKGROUND OF THE INVENTION

This invention relates generally to the field of drug infusion systems. More specifically, it relates to a method and apparatus for compressing or collapsing a compliant or flexible container or reservoir for a liquid drug to cause the contents of the container or reservoir to flow through a delivery tube like under substantially constant pressure.

Many drugs or pharmacologically active medicaments are introduced into a patient's bloodstream or bodily tissues by drug delivery systems that produce a controlled flow of the liquid into the patient's body. Among such systems are intravenous (IV) systems in which the liquid is stored in a bag external to the body and is then conducted into the body (either by an external pump or gravity) through a flexible conduit and an IV needle; and implantable systems, in which a liquid reservoir, a pump, and a delivery tube are implanted in the body. For the purposes of this disclosure, both types of drug delivery systems may be termed "infusion systems".

It is typical in such systems to require a controlled rate of delivery of the liquid. In gravity flow IV systems, for example, a valving mechanism may provide such a controllable flow rate. Other infusion systems employ an infusion pump for this purpose. The infusion pump may be powered by various means. For example, pumps employing a solenoid-actuated mechanism are disclosed in the following U.S. Patents: U.S. Pat. Nos. 4,360,019—Portner et al.; 4,557,726—Reinicke; and 4,594,058—Fischell. Pumps employing a spring-actuated mechanism are disclosed in U.S. Pat. Nos. 4,447,232—Sealfon et al. and 5,328,477—Sitko. Electric motor-driven pumps are disclosed in U.S. Pat. Nos. 5,23,439—Campbell et al. and 5,330,431—Herskowitz. A pump that employs a gas-operated mechanism is disclosed in U.S. Pat. No. 5,242,406—Gross et al. A combination of electromagnetic and spring-actuated means for an infusion pump is disclosed in U.S. Pat. No. 4,274,407—Scarlett.

The typical prior art infusion pump, as exemplified by the above-mentioned references, requires a relatively bulky and/or complex mechanism to provide the desired control over the flow rate. One factor that contributes to the complexity of those infusion pumps that apply a compressive force to a bag-like or bladder-like deformable (compressible) reservoir is the changing geometry of the reservoir as it empties. Specifically, where the pumping mechanism applies a compressive force to the compressible reservoir, the changing geometry of the reservoir results in a change in the area against which the force is applied, thereby changing the applied pressure (force per unit area). Typically, as the reservoir's volume is reduced, the surface area on which the compressive force is applied increases, thereby resulting in a decrease in force per unit area (pressure). Therefore, where it is desired to maintain a substantially constant pressure, or an increasing pressure, for the fluid flow from the reservoir, the pumping mechanism must include means for compensating for the effect of increasing reservoir surface area exposed to the compressive force.

Several of the above-mentioned patents disclose devices that mechanically compress a deformable reservoir bag. See U.S. Pat. Nos. 4,274,407—Scarlett; 4,447,232—Sealfon et al.; 5,232,439—Campbell et al.; 5,242,406—Gross et al.; 5,328,477—Sitko; and 5,330,431—Herskowitz. Of these, U.S. Pat. No. 5,232,439—Campbell et al. most clearly recognizes the problem of compensating for increasing reservoir surface area exposed to the compressive force. The device disclosed in this patent employs motor drive controls to control the movement of a pressure plate against the reservoir bag. U.S. Pat. No. 5,330,431—Herskowitz also recognizes the problem of maintaining constant pressure to the reservoir bag. Like the device in the Campbell et al. patent, the Herskowitz device uses motor drive controls to control the movement of the bag compressing element.

While the prior art has thus addressed the problem of maintaining a substantially constant pressure applied to a deformable reservoir bag in an infusion pump, it has done so with devices that include relatively complex and costly control mechanisms. It would be a marked advance over the prior art to provide an infusion pump that satisfactorily addresses this problem with a relatively simple mechanism that may be manufactured economically, and that is simple to use and easy to maintain in working order. Furthermore, it would be advantageous for such an infusion pump to require no electrical power, so as to avoid the need for changing batteries. In addition, it would be a still further advantage for such an improved pump to accommodate standard pre-filled reservoir bags.

SUMMARY OF THE INVENTION

Broadly, the present invention is a magnetically actuated infusion pump for extracting a flow of liquid from a deformable reservoir (e.g., a bag or a bladder) at a controlled pressure, wherein the reservoir is compressed between a permanent magnet and a platen of magnetizable metal (e.g., a hard ferrous alloy). The magnet and the platen have parallel compressing surfaces, and the reservoir is disposed in the space defined between the two compressing surfaces. Either the magnet or the platen is movable along the axis perpendicular to the plane of the compressing surfaces.

The magnetic force of attraction between the magnet and the platen is inversely proportional to the square of the distance between them. Therefore, when a filled reservoir is placed between the magnet and the platen, the distance between them is at its maximum, and the force of attraction, which provides the force that applies pressure to the reservoir, is at its minimum. At this point in time, the surface area of the reservoir that is in contact with the compressing surfaces is also at its minimum. The magnetic force of attraction divided by this surface area of contact yields the pressure applied to the reservoir.

As the reservoir is compressed by the closing of the space between the platen and the magnet due to the magnetic force of attraction, the contents of the reservoir are displaced therefrom, decreasing its volume as it deformably collapses under the compression. This deformable collapsing increases the surface area of contact, while at the same time the magnetic force of attraction is increasing at a faster rate due to the decreasing distance between the platen and the magnet. Consequently, there is an increase in the force per unit area of contact. As a result, therefore, the pressure applied to the reservoir increases as the reservoir empties.

The ratio of the reservoir bag's total thickness (including its contents) to its surface area of contact, when it is full and at any given time during its emptying, may be termed the "contact aspect ratio" of the bag. A bag that is full or nearly full will usually have a relatively high contact aspect ratio, which decreases as the bag empties. If, when the bag is full, its surface is curved (rather than relatively flat), its contact aspect ratio may be greater than one. In the beginning of the emptying process, the surface area of contact will increase more rapidly than the thickness decreases, yielding a relatively rapidly diminishing contact aspect ratio. Furthermore, the pressure applied to the bag is inversely proportional to the contact surface area, and it is inversely proportional to the square of the thickness. Thus, with the surface area of contact increasing while the bag thickness decreases at the beginning of the emptying process, the pressure applied by the magnetic force increases more rapidly when the contact aspect ratio is relatively high, and increases more slowly when the ratio is low, as the surface area of contact reaches a constant at its maximum. Consequently, for bags having a relatively large contact aspect ratio, springs or linkages may advantageously be added to maintain a substantially linear increase in pressure throughout the emptying process. Alternatively, springs or linkages may be added to maintain a substantially constant or linearly decreasing pressure as the bag empties.

In its simplest form, the invention comprises a two-piece housing having first and second housing portions that are removably attachable to each other to define an internal chamber. Extending from the center of the interior surface of the first housing portion is a cylindrical guide member, terminating in a flattened, disc-like head. Concentrically surrounding the guide member is an annular carrier to which is fastened an annular permanent magnet. The carrier is movable axially with respect to the guide member between a first or proximal position (in which it is seated against the interior surface of the first housing portion), and a second or distal position (in which it abuts against the guide member head). Fixed to the interior surface of the second housing portion is a platen, made of a magnetizable (ferrous) metal alloy.

When the carrier is in its proximal position, a space is defined between the magnet and the platen, in which space a liquid-filled compliant plastic reservoir bag is installed. The bag has an outflow tube, and one of the housing portions (preferably the second) has a passage to its exterior to accommodate the outflow tube.

When a completely full bag is installed, a fraction of its surface area is in contact with the magnet and the platen. The magnetic attraction between the platen and the magnet creates a compressive force against this contact area of the bag. The distance between the platen and the magnet at this point is at its maximum; the magnetic force of attraction is thus at its minimum. The pressure applied to the bag is equal to the magnetic force of attraction divided by the contact area.

As the bag discharges its contents and deformably collapses under the pressure applied by the magnetic force of attraction, the distance between the magnet and the platen decreases, thereby increasing the magnetic force of attraction. The deformable collapsing of the bag, however, brings more of its surface area into contact with the platen and the magnet. Thus, the surface area of contact increases as the magnetic force of attraction increases. Since the magnetic force of attraction is inversely proportional to the square of the distance between the magnet and the platen, while the rate of increase of the surface area of contact decreases as the distance decreases (up to the maximum surface area of contact, after which the surface area of contact remains constant), the compressive force applied per unit area of contact increases. As a result, the pressure applied to the bag increases as the bag empties, with a resultant increase in the pressure of the flow of liquid from the bag. The rate of increase is known (e.g., empirically) for any bag of a given contact aspect ratio.

Other preferred embodiments provide for altering the relationship between the decreasing volume of the bag and the pressure applied to it. In one such embodiment, a coil spring is installed around the guide member, between the proximal side of the carrier and the interior surface of the first housing portion. The spring is at its maximum compression when the carrier is at its proximal position, and thus provides a greater compressive force component when the force of magnetic attraction is at its minimum. The spring component then decreases as the magnetic force component increases as the carrier moves to its distal position. This embodiment, therefore, provides an augmented compressive force at the beginning of the bag discharge process, i.e., when the bag is full and when it is only slightly emptied. Thus, the spring compensates for the increase in the pressure applied by the magnetic force of attraction as the bag is emptied. Consequently, the pressure applied to the bag can be made substantially constant for bags of a given contact aspect ratio, or the pressure can be made to increase or decrease at a known rate as the bag empties.

In another embodiment, an uncompressed coil spring is installed around the guide member between the distal side of the carrier and the guide member head. With this arrangement, the spring exerts a force that acts counter to the magnetic force of attraction, with the counter-acting spring force increasing as the magnetic force increases. This embodiment, therefore, provides a diminished compressive force toward the end of the bag discharge process, i.e., when the bag is nearly empty. Consequently, as with the embodiment described immediately above, the pressure can be maintained substantially constant throughout the emptying process for bags of a given contact aspect ratio, or the pressure can be made to increase or decrease at a known rate as the bag empties.

The compressive force provided by the force of magnetic attraction can be augmented by different magnet arrangements. For example, instead of mounting a single magnet on a carrier, a pair of magnets can be mounted in the housing so as to pivot from their peripheral edges, in "drawbridge" fashion. This arrangement brings a greater portion of the surface area of the bag into contact with the compressive distal surfaces of the magnets, thereby increasing the pressure applied by the force of magnetic attraction throughout the bag discharge process. Alternatively, the force of magnetic attraction can be increased throughout the discharge process by substituting a fixed magnet for the platen, so that the bag is compressed between the movable magnet on the carrier and the fixed magnet in the second housing portion.

Still another preferred embodiment accommodates larger reservoir bags, that would result in such a large separation between the magnet and the platen, when the bag is filled, that the magnetic force of attraction would be too attenuated to initiate the bag discharge process. In this embodiment, a permanent magnet is fixed to the interior surface of the first housing portion. A pivoting linkage, comprising first and second opposed pivot arms is mounted the pi housing. Each of the pivot arms is pivotably mounted in the housing at or near its center point, so that the pivot arms, in a first position, are coincident with a diameter of the housing. The radially innermost ends of the pivot arms are pivotably connected to the center of a magnetizable metal plate, on its distal surface. The radially outermost ends of the pivot arms are attached to the proximal side of a pressure plate, near its peripheral edge.

When the pivot arms are in the first position, the magnetizable metal plate is at its most distal position, spaced from the magnet, and the pressure plate is in its most proximal position, spaced from the interior surface of the second housing portion. A filled reservoir bag is placed between the pressure plate and the interior surface of the second housing portion. The magnetic attraction between the permanent magnet and the magnetizable metal plate causes the metal plate to move toward the magnet, thereby pivoting the pivot arms toward their second position. The pivoting action of the pivot arms toward their second position, in turn, forces the pressure plate distally, toward the interior surface of the second housing portion, thereby applying a pressure to the bag to discharge its contents. As in the other embodiments, the magnetic force of attraction, and thus the compressive force applied to the bag through the linkage, increases as the contact area to which this force is applied also increases, thereby maintaining a substantially constant pressure on the bag. Alternatively, the linkage can be fashioned to provide a known rate of increase in pressure.

It will thus be appreciated that the present invention provides an infusion pump that is capable of delivering a liquid at an increasing, decreasing, or a substantially constant pressure, and that this result is accomplished with a device that can be simply and economically manufactured. Moreover, the relatively simple mechanical mechanism employed in the invention is both reliable and durable, and it requires no electrical power source or complex control mechanism to achieve its results. These and other advantages of the invention will be more readily understood from the detailed description that follows.

BRIEF DESCRIPTION OF THE DRAWINGS

FIG. 8 is a cross-sectional view of an infusion pump in accordance with a fifth preferred embodiment of the invention, showing the pump with a full reservoir bag installed in it;

FIG. 9 is a cross-sectional view of the fifth preferred embodiment, similar to that of FIG. 8, but showing the infusion pump after the reservoir bag has been substantially emptied of its contents;

FIG. 10 is a cross-sectional view of a modified form of the first preferred embodiment, showing the infusion pump with a full reservoir bag installed in it;

FIG. 11 is a cross-sectional view of the infusion pump of FIG. 10, but showing the pump after the reservoir bag has been substantially emptied of its contents;

FIG. 12 is a cross-sectional view of an infusion pump in accordance with a sixth preferred embodiment of the invention, showing the pump with a full reservoir bag installed in it; and FIG. 13 is a cross-sectional view of the sixth preferred embodiment, similar to that of FIG. 12, but showing the pump after the reservoir bag has been substantially emptied of its contents.

DETAILED DESCRIPTION OF THE PREFERRED EMBODIMENTS

Figure 1:
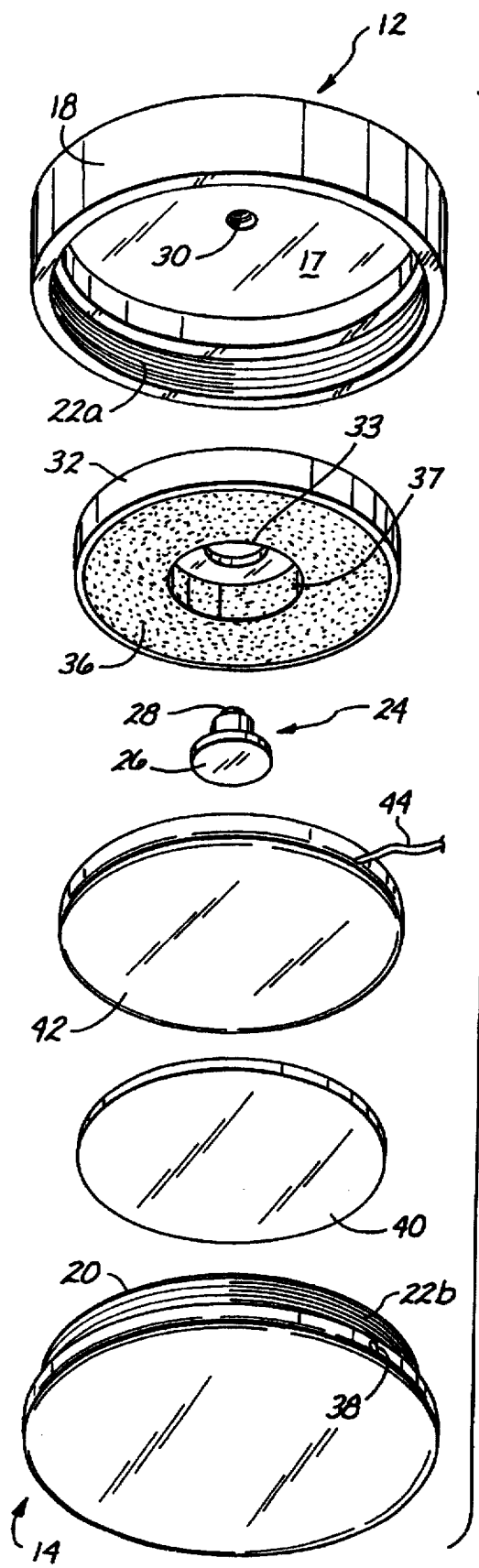
FIG. 1 is an exploded perspective view of an infusion pump in accordance with a first preferred embodiment of the invention.
Figure 2:
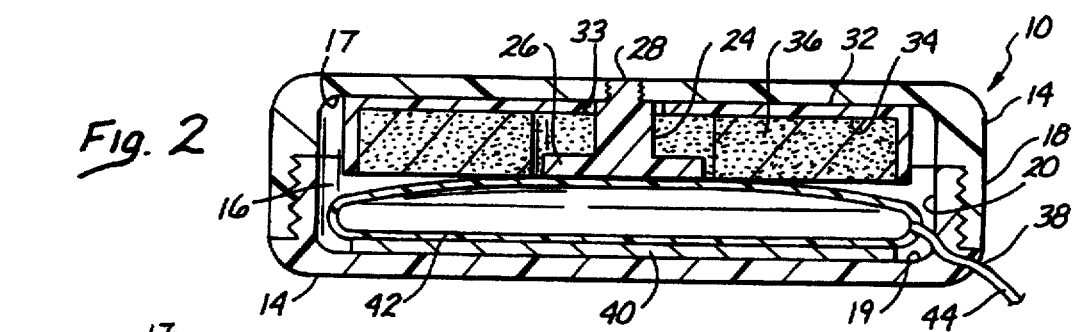
FIG. 2 is a cross-sectional view of the embodiment of FIG. 1, showing the infusion pump with a full reservoir bag installed in it.
Figure 3:
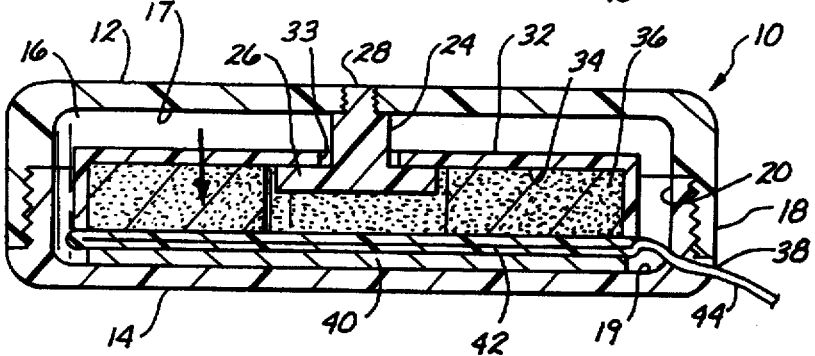
FIG. 3 is a cross-sectional view of the first preferred embodiment, similar to that of FIG. 2, but showing the infusion pump after the reservoir bag has been substantially emptied of its contents.

Referring first to FIGS. 1, 2, and 3, a magnetic infusion pump 10, in accordance with a first preferred embodiment of the present invention, includes a substantially puck-shaped housing that comprises an upper or proximal housing portion 12 and a lower or distal housing portion 14 that are removably attachable to each other to define an internal chamber 16. (For the purpose of this specification, the terms "proximal" and "distal" are preferred and will hereinafter be used, instead of "upper" and "lower", respectively, since, as will be appreciated from the description below, the orientation of the invention in use is arbitrary.) The proximal housing portion 12 defines a proximal interior surface 17, and it has a distally-extending first peripheral flange 18. The distal housing portion 14 defines a distal interior surface 19, and it has a proximally-extending second peripheral flange 20 that removably mates with the first flange 18 on the proximal housing portion 12. Preferably, the first flange 18 and the second flange 20 include complementary threads 22a, 22b (as best shown in FIG. 1), for the removable attachment of the proximal and distal housing portions.

Extending inwardly from the proximal interior surface 17 of the proximal housing portion 12 is a substantially cylindrical guide member 24, terminating in a distal end having a flattened, enlarged-diameter, disc-like head 26. The guide member 24 may advantageously be removably attached to the proximal housing portion 12 by an externally-threaded end portion 28 that screws into an internally-threaded hole 30 in the center of the proximal housing portion 12. Concentrically surrounding the guide member 24 is an annular carrier 32 having a central aperture 33 that is somewhat larger in diameter than the main portion of the guide member 24, but smaller in diameter than the guide member head 26. The carrier 32 has a flat distal surface 34, to which is fixed (as by a suitable adhesive) an annular permanent magnet 36. The magnet 36 has a central aperture 37 (FIG. 1) that is larger in diameter than the guide member head 26. The carrier 32 and the magnet 36 are axially movable along the guide member 24 between a first or proximal position (FIG. 2), in which the carrier 32 abuts against the proximal interior surface 17 of the proximal housing portion 12, and a second or distal position (FIG. 3), in which the carrier 32 abuts against the head 26 of the guide member 24. In the proximal position of the carrier 32 and the magnet 36, the distance between the magnet 36 and the platen 40 is at its maximum, while in the distal position of the carrier 32 and the magnet 36, the distance between the magnet 36 and the platen 40 is at its minimum.

The distal housing portion 14 includes a passage 38 from the interior chamber 16 to the exterior of the housing. Fixed to the distal interior surface 19 of the distal housing portion 14 is a platen 40 of a magnetizable (ferrous) metal alloy.

The proximal and distal housing portions are separated for the installation of a collapsible reservoir bag 42, filled with a pharmacologically active liquid. When the proximal and distal housing portions are joined to each other, the bag 42 occupies the space defined between the platen 40 and the magnet 36, with the carrier 32 being displaced (by the bag 42) to its first or proximal position, as shown in FIG. 2. The bag 42 includes an outflow tube 44 that is inserted through the passage 38.

When a completely full bag 42 is installed, a fraction of its surface area is in contact with the magnet 36 and the platen 40. The magnetic attraction between the platen 40 and the magnet 36 creates a compressive force against this contact area of the bag 42. The distance between the platen 40 and the magnet 36 at this point is at its maximum; the magnetic force of attraction is thus at its minimum. The pressure applied to the bag 42 is equal to the magnetic force of attraction divided by the contact area.

As the bag 42 discharges its contents and deformably collapses under the pressure applied by the magnetic force of attraction, the magnet 36, carried by the carrier 32, moves toward the second (distal) position shown in FIG. 3. As the magnet 36 moves distally, the distance between the magnet 36 and the platen 40 decreases, thereby increasing the magnetic force of attraction. The deformable collapsing of the bag 42, however, brings more of its surface area into contact with the platen 40 and the magnet 36. Thus, the surface area of contact increases as the magnetic force of attraction increases. Since the magnetic force of attraction is inversely proportional to the square of the distance between the magnet 36 and the platen 40, while the rate of increase of the surface area of contact decreases as the distance decreases (up to the maximum surface area of contact, after which the surface area of contact remains constant), the compressive force applied per unit area of contact increases. As a result, the pressure applied to the bag 42 increases as the bag 42 empties, with a resultant increase in the pressure of the flow of liquid from the bag 42 through the outflow tube 44. The rate of increase is known (e.g., empirically) for any bag 42 of a given contact aspect ratio.

A modification of the above-described embodiment is shown in FIGS. 10 and 11. In this modification, a modified platen 40' includes a central portion surrounded by a stepped peripheral portion 45, wherein the distance from the proximal surface of the stepped peripheral portion 45 to the surface of the central portion of the platen 40' (that is, the height of the stepped portion 45) is approximately equal to the thickness of a completely emptied bag 42. With the stepped peripheral portion 45 decreasing the effective distance between the platen 40' and the magnet 36, the magnetic force of attraction is stronger, thereby increasing the compressive force (and thus the pressure) applied to the bag. This modification can be incorporated as well into the embodiments of FIGS. 4, 6, 8, and 9, described below.

Figure 4:
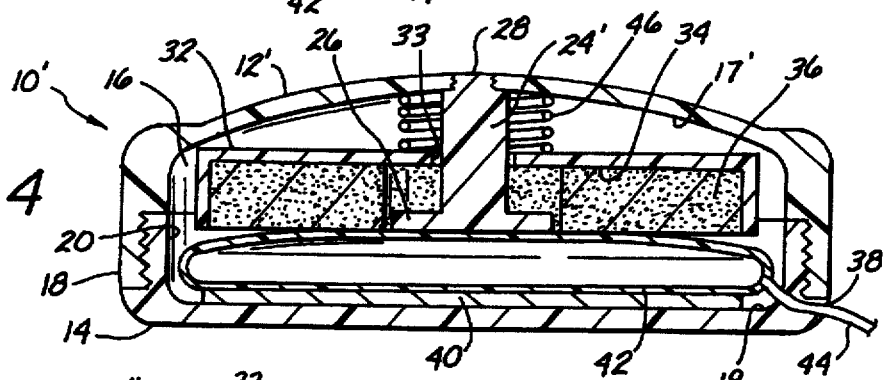
FIG. 4 is a cross-sectional view of an infusion pump in accordance with a second preferred embodiment of the invention.

FIG. 4 illustrates a magnetic infusion pump 10', in accordance with a second preferred embodiment of the invention. This embodiment is similar to the above-described first embodiment, except that a longer guide member 24' is employed, and a coil spring 46 is installed around the guide member 46, between the proximal side of the carrier 32 and the proximal interior surface 17' of the proximal housing portion 12', which may advantageously be somewhat dome-shaped, as shown, to accommodate the longer guide member 24'.

The spring 46 biases the carrier toward the second (distal) position, and it is at its maximum compression when the carrier 32 is at its proximal position (shown in FIG. 4), and thus provides a greater compressive force component when the force of magnetic attraction is at its minimum. The spring component of the compressive force then decreases as the magnetic force component increases, as the magnet 36 on the carrier 32 moves to its distal position. This embodiment, therefore, provides an augmented compressive force at the beginning of the bag discharge process, i.e., when the bag 42 is full and when it is only slightly emptied. Thus, the spring 46 compensates for the increase in the pressure applied by the magnetic force of attraction as the bag 42 is emptied. Consequently, the pressure applied to the bag 42 can be made substantially constant for bags of a given contact aspect ratio, or the pressure can be made to increase or decrease at a known rate as the bag 42 empties.

Figure 5:
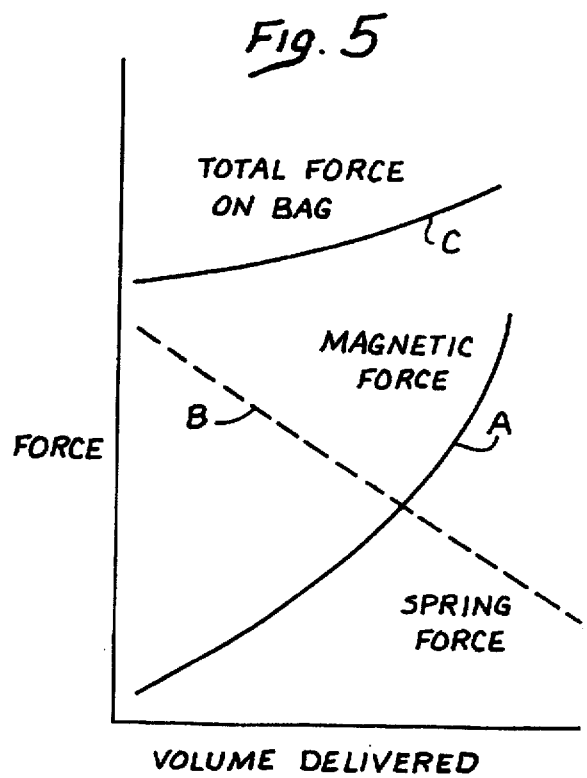
FIG. 5 is graphical representation of the forces applied to the reservoir bag in the embodiment of FIG. 4.

A graphic illustration of the operation of the embodiment of FIG. 4 is shown in FIG. 5, which depicts three curves of compressive force applied to the bag 42 versus volume delivered from the bag 42. Curve A represents the increase in the force of magnetic attraction as the bag 42 empties, while curve B represents the decrease in the compressive force applied by the spring 46 as the bag 42 empties. The resultant total compressive force applied to the bag 42 is represented by curve C, which shows that the total compressive force applied to the bag 42 increases slightly as the bag 42 empties. Since the surface area of contact of the bag 42 increases (at least near the beginning of the emptying process), the pressure applied to the bag 42 (and thus to the flow of liquid from it) will remain substantially constant throughout the emptying process.

The spring 46 can be replaced to change the spring constant, and thus the slope of the curve B. Changing the slope of curve B, in turn, changes the slope of the curve C. Consequently, the pressure applied to the bag 42 can be made to remain substantially constant for bags with differing contact aspect ratios, or the pressure can be made to increase or decrease in a known, controlled manner throughout the bag emptying process.

Figure 6:
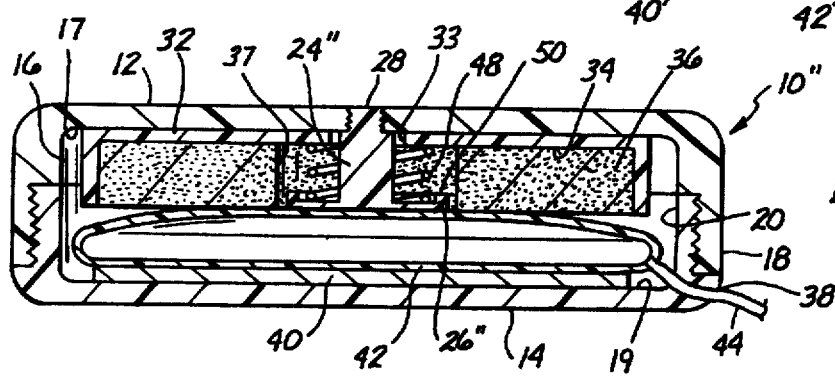
FIG. 6 is a cross-sectional view of an infusion pump in accordance with a third preferred embodiment of the invention.

An infusion pump 10", in accordance with a third preferred embodiment of the invention, is shown in FIG. 6. In this embodiment, an uncompressed coil spring 48 is installed around a guide member 24", spaced radially inwardly from the periphery of the magnet aperture 37. One end of the spring 48 is seated against the distal surface of the carrier 32, and the other end of the spring 48 is seated against the proximal side of a guide member head 26". The guide member head 26" is advantageously provided with a peripheral lip 50, which forms a seat on the proximal side of the guide member head 26" for the spring 48. With this arrangement, the spring 48 exerts a force that tends to push the carrier 32 toward its first (proximal) position, and thus acts counter to the magnetic force of attraction. The counteracting (proximally-directed) spring force increases as the magnet 36 and the carrier 32 travel to the second (distal) position as the bag 42 empties. Thus, the compressive force component applied by the spring 48 decreases as the magnetic force component increases. This embodiment, therefore, provides a diminished compressive force toward the end of the bag discharge process, i.e., when the bag 42 is nearly empty. Consequently, as with the embodiment of FIG. 4, the pressure can be maintained substantially constant throughout the emptying process for bags of a given contact aspect ratio, or the pressure can be made to increase or decrease at a known rate as the bag 42 empties, depending on the spring constant.

Figure 7:
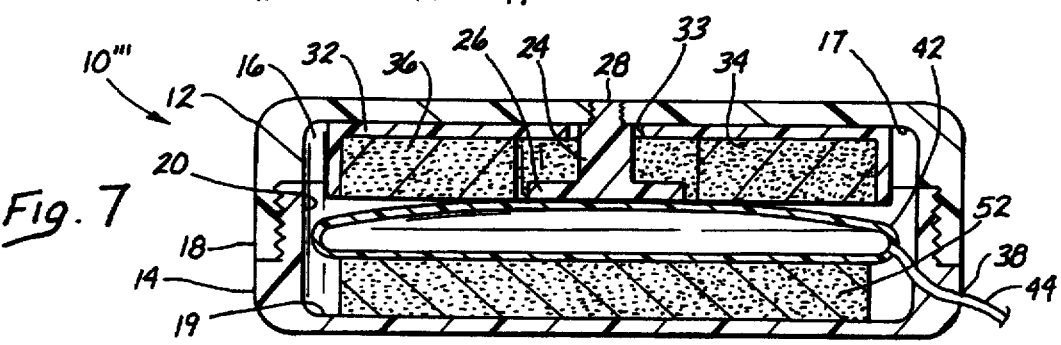
FIG. 7 is a cross-sectional view of an infusion pump in accordance with a fourth preferred embodiment of the invention.

FIG. 7 illustrates a magnetic infusion pump 10'", in accordance with a fourth preferred embodiment of the invention. In this embodiment, the platen is a fixed permanent magnet 52, attached (as by a suitable adhesive) to the distal interior surface 19 of the distal housing portion 14. This double magnet embodiment provides an increased magnetic force of attraction (as compared with the above-described single magnet embodiments) throughout the bag emptying process. This embodiment may be advantageous in applications in which higher fluid pressures are desired, or where larger volume bags are used, or where bags with higher contact aspect ratios are employed.

A magnetic infusion pump 60, in accordance with a fifth preferred embodiment of the invention, is shown in FIGS. 8 and 9. This embodiment includes a proximal housing portion 62 and a distal housing portion 64 that are removably attachable to one another, by means such as threads 66, to form a housing that defines an interior chamber 68. The proximal housing portion 62 preferably has a convex, somewhat dome-shaped configuration, with a central orifice 70. The orifice 70 accommodates an outflow tube 72 extending from a collapsible reservoir bag 74.

The distal housing portion 64 has a distal interior surface 75, to which is fixed (as by a suitable adhesive), a platen 76 of a magnetizable metal alloy. As illustrated, the platen 76 may incorporate the stepped edge configuration, described above in connection with FIGS. 10 and 11, wherein the platen 76 has a central portion 78 and a stepped peripheral portion 79 surrounding the central portion 78, and extending radially inwardly from the peripheral edge of the platen 76.

Fixed to the peripheral edge of the platen 76, at diametrically opposite positions, are a pair of hinges 80. Each hinge 80 has a fixed portion attached to the platen 76, and a movable portion, to which is attached a permanent magnet 82. The magnets 82 are thus pivotable at their hinged edges, in "drawbridge" fashion, from a first (proximal) position (FIG. 8) to a second (distal) position (FIG. 9). In the second position, the magnets 82 are more distantly spaced from the central portion 78 of the platen 76 than they are from the peripheral portion 79, the spacing between the magnets 82 and the central portion 78 of the platen 76 being sufficient to accommodate the thickness of the collapsed bag 74.

As compared with the single magnet embodiments described above in connection with FIGS. 1 through 4, 6, 10, and 11, this arrangement reduces the effective distance between the magnets 82 and the platen 76, thereby increasing the magnetic force of attraction. Furthermore, as compared with the above described single magnet embodiments, a greater contact surface area between the filled bag 74 and the magnets 82 is achieved. The net result is that smaller magnets can be used to attain a desired pressure.

FIGS. 12 and 13 illustrate a magnetic infusion pump 90, in accordance with a sixth preferred embodiment of the present invention. This embodiment accommodates larger reservoir bags, that would result in such a large separation between the magnet and the platen, when the bag is filled, that the magnetic force of attraction would be too attenuated to initiate the bag discharge process.

As in the previously described embodiments, this embodiment includes a housing comprising a proximal housing portion 92, having a proximal interior surface 93, and a distal housing portion 94, having a distal interior surface 95. The proximal and distal housing portions are removably attached to each other, as by threads 96. A permanent magnet 98 is attached to the proximal interior surface 93. A passage 99 is formed through the distal housing portion 94 to accommodate an outflow tube 100 from a collapsible reservoir bag 101 that is installed in the housing so as to rest on the distal interior surface 95.

A pivoting linkage, comprising first and second opposed pivot arms 102, is mounted in the housing. Each of the pivot arms 102 is pivotably supported in the proximal housing portion 92 by a pivot pin 104 at or near the center point of the pivot arm 102, so that the pivot arms 102, in a first position (FIG. 12), are coincident with a diameter of the housing, lying essentially parallel to the magnet 98.

The radially innermost ends of the pivot arms 102 are pivotably connected, by a first pivot mount 106, to the center of a magnetizable metal plate 108, on its distal surface. The radially outermost end of each of the pivot arms 102 is pivotably connected, by a second pivot mount 110, to the proximal side of a pressure plate 112, each of the second pivot mounts 110 being located near diametrically opposite portions of the peripheral edge of the pressure plate 112.

When the pivot arms 102 are in the first position (FIG. 12), the magnetizable metal plate 108 is at its most distal position, at maximum distance from the magnet 98, and the pressure plate 112 is in its most proximal position, at maximum distance from the distal interior surface 95 of the distal housing portion 94. A filled reservoir bag 101 is placed between the pressure plate 112 and the distal interior surface 95. The magnetic attraction between the permanent magnet 98 and the magnetizable metal plate 108 causes the metal plate 108 to move proximally, toward a proximal position of minimum distance from the magnet 98, thereby pivoting the pivot arms 102 toward their second position (FIG. 13), in which they define a triangle with the pressure plate 112. The pivoting action of the pivot arms 102 toward their second position, in turn, forces the pressure plate 112 distally, toward a distal position of minimum distance from the distal interior surface 95 of the distal housing portion 94, thereby applying a pressure to the bag 101 to discharge its contents. The linkage thus allows the pressure plate 112 to travel a distance that is a multiple of the width of the magnetic gap between the metal plate 108 and the magnet 98 when the linkage is in the first position. Thus, the linkage allows the device to accommodate a bag 101 which, when full, has a thickness that is as great as that multiple of the magnetic gap width.

As in the other embodiments, the magnetic force of attraction, and thus the compressive force applied to the bag 101 through the linkage, increases as the contact area to which this force is applied also increases, thereby maintaining a substantially constant pressure on the bag 101. Alternatively, the linkage can be fashioned to provide a known rate of increase in pressure.

From the foregoing description, it will be appreciated that the present invention, in its various embodiments, offers an infusion pump that is capable of providing controllable infusion pressures by means of a relatively simple magnetic and mechanical mechanism. The invention thus requires no electrical power, nor does it require electronic means for controlling its drive mechanism, and, accordingly, is relatively simple and economical to manufacture. Furthermore, the present invention is easy to use and to maintain in proper working order.

The preferred embodiments described herein are exemplary only, and further modifications and variations may suggest themselves to those skilled in the pertinent arts. For example, any of a variety of spring and/or linkage arrangements may be employed, either to accommodate reservoir bags of different sizes and configurations, or to achieve whatever compressive force-versus-volume delivered curve (FIG. 5) is desired in a particular application. Such variations and modifications should be considered within the spirit and scope of the present invention, as defined in the claims that follow.

What is claimed is:

1. An infusion pump for providing a pressurized liquid flow from a collapsible, deformable, liquid-filled reservoir bag, the pump comprising:

a housing comprising first and second housing portions removably attachable to each other and defining an interior chamber sized to receive and hold a collapsible, deformable, liquid-filled reservoir bag;

a platen of magnetizable metal disposed within the housing; and magnet means disposed within the housing for movement between a first position of maximum distance from the platen and a second position of minimum distance from the platen;

wherein a reservoir bag seated on the plate is compressed by the movement of the magnet means from the first position to the second position in response to the force of magnetic attraction between the magnet means and the platen.

2. The infusion pump of claim 1, further comprising a spring disposed between the magnet means and an interior surface of the housing so as to bias the magnet means toward the second position.

3. The infusion pump of claim 1, wherein the magnet means includes a substantially annular magnet disposed concentrically around a substantially cylindrical guide member having a first end fixed to an interior surface of the housing and a second end extending into the chamber, and wherein the infusion pump further comprises:

a spring disposed concentrically between the annular magnet and the guide member so as to bias the magnet means toward the first position.

4. The infusion pump of claim 1, wherein the platen has a peripheral edge, and wherein the magnet means comprises first and second magnets, each having a first edge that is pivotably connected to the peripheral edge of the platen, whereby the first and second magnets are pivotable at their respective first edges between the first position and the second position.

5. The infusion pump of claim 1, wherein the platen includes a magnet.

6. The infusion pump of claims 1, 2, 3, 4, or 5 wherein the platen comprises:

a central portion; and a stepped peripheral portion surrounding the central portion, the peripheral portion being closer to the magnet means than is the central portion.

7. An infusion pump for providing a pressurized liquid flow from a collapsible, deformable, liquid-filled reservoir bag, the pump comprising:

a housing defining an interior chamber sized to receive and hold a collapsible, deformable, liquid-filled reservoir bag, the housing including a first housing portion having a proximal interior surface and a second housing portion having a distal interior surface, the first and second housing portions being removably attachable to each other;

a platen of magnetizable metal fixed to the distal interior surface; and magnet means disposed within the housing for movement between a first position of maximum distance from the platen and a second position of minimum distance from the platen;

wherein a reservoir bag seated on the platen is compressed by the movement of the magnet means from the first position to the second position in response to the force of magnetic attraction between the magnet means and the platen.

8. The infusion pump of claim 7, further comprising a guide member extending distally into the interior chamber from the proximal interior surface, wherein the magnet means comprises:

a permanent magnet disposed on the guide member for axial translation between the first position and the second position.

9. The infusion pump of claim 8, further comprising:

a spring, disposed between the proximal interior surface and the magnet, that biases the magnet toward the second position.

10. The infusion pump of claim 7, further comprising a substantially cylindrical guide member extending distally into the interior chamber from the proximal interior surface, and having a distal end formed as an enlarged-diameter head with a proximal surface, and wherein the magnet means comprises:

a magnet carrier disposed concentrically around the guide member and having flat distal surface surrounding a central aperture that is larger than the diameter of the guide member and smaller than the diameter of the head; and a permanent magnet fixed to the distal surface of the magnet carrier and having a central aperture with a diameter that is larger than the diameter of the head.

11. The infusion pump of claim 10, further comprising:

a spring disposed concentrically around the guide member and seated between the distal surface of the magnet carrier and the proximal surface of the head, so that the spring biases the carrier toward the first position.

12. The infusion pump of claim 7, wherein the platen includes a permanent magnet.

13. The infusion pump of claim 7, wherein the platen has a peripheral edge, and wherein the magnet means comprises first and second magnets, each having a first edge that is pivotably connected to the peripheral edge of the platen, whereby the first and second magnets are pivotable at their respective first edges between the first position and the second position.

14. The infusion pump of claims 7, 8, 9, 10, 11, 12, or 13, wherein the platen comprises:

a central portion; and a stepped peripheral portion surrounding the central portion, the peripheral portion being closer to the magnet means than is the central portion.

15. An infusion pump for providing a pressurized liquid flow from a collapsible, deformable, liquid-filled reservoir bag, the pump comprising:

a housing defining an interior chamber sized to receive and hold a collapsible, deformable, liquid-filled reservoir bag, the housing including a first housing portion having a proximal interior surface and a second housing portion having a distal interior surface, the first and second housing portions being removably attachable to each other;

a pressure plate disposed within the housing and movable between a first position of maximum distance from the distal interior surface and a second position of minimum distance from the distal interior surface; and magnetic means, disposed within the housing, for moving the pressure plate between the first and second positions by the force of magnetic attraction;

whereby a reservoir bag disposed within the housing between the pressure plate and the distal interior surface is compressed by the movement of the pressure plate from the first position to the second position.

16. The infusion pump of claim 15, wherein the magnetic means comprises:

a permanent magnet fixed to the proximal interior surface;

a magnetizable metal plate disposed between the magnet and the pressure plate and movable between a distal position of maximum distance from the magnet and a proximal position of minimum distance from the magnet; and a pivoting linkage connecting the magnetizable metal plate and the pressure plate so that the movement of the magnetizable metal plate from the distal position to the proximal position in response to the force of magnetic attraction causes the pressure plate to move from the first position to the second position.

17. The infusion pump of claim 16, wherein pressure plate has a peripheral edge, and wherein the pivoting linkage comprises:

first and second opposed pivot arms, each having a radially innermost end and a radially outermost end, each of the pivot arms being pivotably supported near its center point within the housing;

first pivot means pivotably connecting the radially innermost end of each of the pivot arms to the approximate center of the magnetizable metal plate; and second pivot means pivotably connecting the radially outermost end of each of the pivot arms to pressure plate near diametrically opposite portions of its peripheral edge;

wherein the pivot arms are movable between a first position, in which they lie substantially parallel with the magnet, and a second position, in which they define a triangle with the pressure plate, the first position of the pivot arms coinciding with the first position of the pressure plate and the distal position of the magnetizable metal plate, and the second position of the pivot arms coinciding with the second position of the pressure plate and the proximal position of the magnetizable metal plate.

18. An infusion pump for providing a pressurized liquid flow from a collapsible, deformable, liquid-filled reservoir bag, the pump comprising:

a housing defining an interior chamber sized to receive and hold a collapsible, deformable, liquid-filled reservoir bag, the housing including a first housing portion having a proximal interior surface and a second housing portion having a distal interior surface, the first and second housing portions being removably attachable to each other;

a platen of magnetizable metal fixed to the distal interior surface and having a peripheral edge; and first and second magnets disposed within the housing for movement between a first position of maximum distance from the platen and a second position of minimum distance from the platen, each of the magnets having a pivoting edge that is pivotably connected to the peripheral edge of the platen, whereby the first and second magnets are pivotable at their respective pivoting edges between the first position and the second position;

wherein a reservoir bag seated on the platen is compressed by the movement of the first and second magnets from the first position to the second position in response to the force of magnetic attraction between the first and second magnets and the platen.

19. The infusion pump of claim 18, wherein the platen has first and second diametrically-opposed edge portions, and wherein the first magnet is pivotably connected to the first edge portion and the second magnet is pivotably connected to the second edge portion.

20. The infusion pump of claim 1, further comprising:

a first hinge having a fixed portion attached to the first edge portion, and a movable portion attached to the pivoting edge of the first magnet; and a second hinge having a fixed portion attached to the second edge portion, and a movable portion attached to the pivoting edge of the second magnet.

21. The infusion pump of claims 18, 19, or 20, wherein the platen comprises:

a central portion; and a stepped peripheral portion surrounding the central portion, the peripheral portion extending radially inwardly from the peripheral edge, whereby the central portion is more distantly spaced from the first and second magnets than is the peripheral portion when the first and second magnets are in their second position.

22. An infusion pump for providing a pressurized liquid flow from a collapsible, deformable, liquid-filled reservoir bag, the pump comprising:

a housing defining an interior chamber sized to receive and hold a collapsible, deformable, liquid-filled reservoir bag, the housing including a first housing portion having a proximal interior surface and a second housing portion having a distal interior surface, the first and second housing portions being removably attachable to each other;

a platen of magnetizable metal fixed to the distal interior surface;

a guide member extending distally into the interior chamber from the proximal interior surface, and having a distal end;

a magnet disposed on the guide member for axial translation between a first position of maximum distance from the platen and a second position of minimum distance from the platen; and a spring, disposed between the proximal interior surface and the magnet, that biases the magnet toward the second position.

23. The infusion pump of claim 22, further comprising:

an enlarged-diameter head formed on the distal end of the guide member, the head having a proximal surface; and a magnet carrier disposed concentrically around the guide member and having flat distal surface surrounding a central aperture that is larger than the diameter of the guide member and smaller than the diameter of the head, wherein the magnet is fixed to the distal surface of the magnet carrier and has a central aperture with a diameter that is larger than the diameter of the head.

24. The infusion pump of claim 23, wherein the spring is disposed concentrically around the guide member and is seated between the magnet carrier and the proximal interior surface of the first housing portion, so that the spring biases the carrier toward the second position.

25. The infusion pump of claims 22, 23, or 24, wherein the platen includes a permanent magnet.

26. The infusion pump of claims 22, 23, or 24, wherein the platen comprises:

a central portion; and a stepped peripheral portion surrounding the central portion, the peripheral portion being closer to the magnet than is the central portion.

27. The infusion pump of claim 26, wherein the platen includes a permanent magnet.

28. An infusion pump for providing a pressurized liquid flow from a collapsible, deformable, liquid-filled reservoir bag, the pump comprising:

a housing defining an interior chamber sized to receive and hold a collapsible, deformable, liquid-filled reservoir bag, the housing including a first housing portion having a proximal interior surface and a second housing portion having a distal interior surface, the first and second housing portions being removably attachable to each other;

a platen of magnetizable metal fixed to the distal interior surface;

a guide member extending distally into the interior chamber from the proximal interior surface, and having a distal end formed as an enlarged-diameter head with a proximal surface;

a magnet carrier disposed concentrically around the guide member and having flat distal surface surrounding a central aperture that is larger than the diameter of the guide member and smaller than the diameter of the head, the magnet carrier being axially movable on the guide member between a first position of maximum distance from the platen and a second position of minimum distance from the platen;

a magnet fixed to the distal surface of the magnet carrier and having a central aperture with a diameter that is larger than the diameter of the head; and a spring, disposed concentrically around the guide member and seated between the distal surface of the magnet carrier and the proximal surface of the head, that biases the magnet toward the first position.

29. The infusion pump of claim 28, wherein the platen comprises:

a central portion; and a stepped peripheral portion surrounding the central portion, the peripheral portion being closer to the magnet than is the central portion.

30. The infusion pump of claim 28, or 29, wherein the platen includes a permanent magnet.

* * * * *